(12) United States Patent
Rainaldi

(10) Patent No.: US 11,568,166 B1
(45) Date of Patent: Jan. 31, 2023

(54) SUGGESTING BEHAVIORAL ADJUSTMENTS BASED ON PHYSIOLOGICAL RESPONSES TO STIMULI ON ELECTRONIC DEVICES

(71) Applicant: Verily Life Sciences LLC, Mountain View, CA (US)

(72) Inventor: Erin Rainaldi, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 507 days.

(21) Appl. No.: 16/521,509

(22) Filed: Jul. 24, 2019

Related U.S. Application Data

(60) Provisional application No. 62/711,258, filed on Jul. 27, 2018.

(51) Int. Cl.
| | |
|---|---|
| *G06K 9/00* | (2022.01) |
| *H04W 4/21* | (2018.01) |
| *G06V 20/40* | (2022.01) |
| *G06V 40/20* | (2022.01) |
| *A61B 5/00* | (2006.01) |
| *A61B 5/145* | (2006.01) |
| *H04W 4/80* | (2018.01) |

(Continued)

(52) U.S. Cl.
CPC ......... *G06K 9/00496* (2013.01); *G06V 20/40* (2022.01); *G06V 40/23* (2022.01); *H04W 4/21* (2018.02); *A61B 5/14532* (2013.01); *A61B 5/7264* (2013.01); *G06T 7/20* (2013.01); *G06V 20/44* (2022.01); *G16H 10/60* (2018.01); *H04W 4/80* (2018.02)

(58) Field of Classification Search
CPC .......... G06K 9/00496; G06K 9/00342; G06K 9/00711; G06K 2009/00738; H04W 4/21; H04W 4/80; A61B 5/14532; A61B 5/7264; G06T 7/20; G16H 10/60
See application file for complete search history.

(56) References Cited

U.S. PATENT DOCUMENTS

| | | | |
|---|---|---|---|
| 7,490,031 B1 * | 2/2009 | Qiu ........................... | G06F 8/38 703/22 |
| 10,006,896 B2 * | 6/2018 | Fernstrom .............. | G01N 33/02 |

(Continued)

FOREIGN PATENT DOCUMENTS

WO      2014066871 A1      5/2014

*Primary Examiner* — Qun Shen
(74) *Attorney, Agent, or Firm* — Perkins Coie LLP

(57) ABSTRACT

Introduced here are health management platforms able to monitor changes in the health state of a subject based on the context of digital activities performed by, or involving, the subject. Initially, a health management platform can identify a physiological response by examining physiological data associated with a subject. Then, the health management platform can identify a stimulus presented by an electronic device that provoked the physiological response by examining contextual data associated with the subject. The contextual data may be in the form of a screenshot of a computer program in use by the subject during the physiological response. In some embodiments, the health management platform prompts the subject to specify whether the physiological response is a positive physiological response that resulted in an upward shift in health or a negative physiological response that resulted in a downward shift in health.

18 Claims, 8 Drawing Sheets

(51) Int. Cl.
*G16H 10/60* (2018.01)
*G06T 7/20* (2017.01)

(56) References Cited

U.S. PATENT DOCUMENTS

| | | | |
|---|---|---|---|
| 2009/0220136 A1* | 9/2009 | Bova | A61B 6/5247 |
| | | | 382/131 |
| 2015/0127737 A1 | 5/2015 | Thompson et al. | |
| 2015/0220157 A1* | 8/2015 | Marggraff | G06F 3/0485 |
| | | | 345/156 |
| 2016/0151022 A1* | 6/2016 | Berlin | A61B 5/7246 |
| | | | 600/301 |
| 2017/0262697 A1 | 9/2017 | Kaps et al. | |
| 2017/0340270 A1* | 11/2017 | Ganesh | A61B 5/4836 |
| 2018/0122509 A1* | 5/2018 | Christiansson | G16H 10/60 |
| 2019/0262724 A1* | 8/2019 | Trombetta | A63F 13/86 |

\* cited by examiner

500

501
Acquire physiological data associated with a subject

502
Detect a physiological response by examining the physiological data

503
Identify a stimulus responsible for causing the physiological response by examining contextual data associated with the subject

504
Create a notification that prompts the subject to provide feedback specifying whether the physiological response corresponds to an upward or downward shift in health

505
Generate a digital record that links the stimulus, physiological response, feedback, and/or shift in health

506
Perform an action with respect to another instance of the stimulus based on the feedback

Acquire physiological data generated by a first electronic device that monitors physical activity of a subject

602

Detect a physiological event by parsing the physiological data

603

Identify a stimulus responsible for causing the physiological event by examining contextual data generated by a second electronic device that monitors digital activity of the subject

604

Generate a notification that requests an individual provide feedback indicating whether the physiological event corresponds to an upward shift in health or a downward shift in health

605

Receive the feedback from the individual

606

Determine that another instance of the stimulus will exist for an interval of time

607

Perform an action with respect to the other instance of the stimulus based on the feedback

FIGURE 6

SUGGESTING BEHAVIORAL ADJUSTMENTS BASED ON PHYSIOLOGICAL RESPONSES TO STIMULI ON ELECTRONIC DEVICES

CROSS-REFERENCE TO RELATED APPLICATIONS

This application claims priority to U.S. Provisional Application No. 62/711,258, titled "Suggesting Behavioral Adjustments Based on Physiological Responses to Stimuli on Electronic Devices" and filed on Jul. 27, 2018, which is incorporated by reference herein in its entirety.

TECHNICAL FIELD

Various embodiments concern computer programs and associated computer-implemented techniques for identifying the stimuli responsible for causing heightened physiological responses.

BACKGROUND

Contemporary research has begun exploring how stimuli presented by electronic devices affect the health state. Such research has considered emotion as a predictor of media selection, an outcome of media exposure, a mediator of other psychological/behavioral outcomes resulting from media exposure, etc. For example, several studies have examined the emotional consequences of using social media (e.g., photo-sharing social networking services, video-sharing social networking services, and micro-blogging social networking services). These studies have shown that the use of social media can cause positive and negative feelings, which can facilitate or hinder the development of social capital and social connectedness.

BRIEF DESCRIPTION OF THE DRAWINGS

Various features of the technology will become more apparent to those skilled in the art from a study of the Detailed Description in conjunction with the drawings. Embodiments of the technology are illustrated by way of example and not limitation in the drawings, in which like references may indicate similar elements.

FIG. 5 depicts a flow diagram of a process for identifying the stimuli responsible for causing a subject to experience heightened physiological responses.

FIG. 6 depicts a flow diagram of a process for proactively regulating exposure to stimuli responsible for provoking physiological responses.

Figure 1:
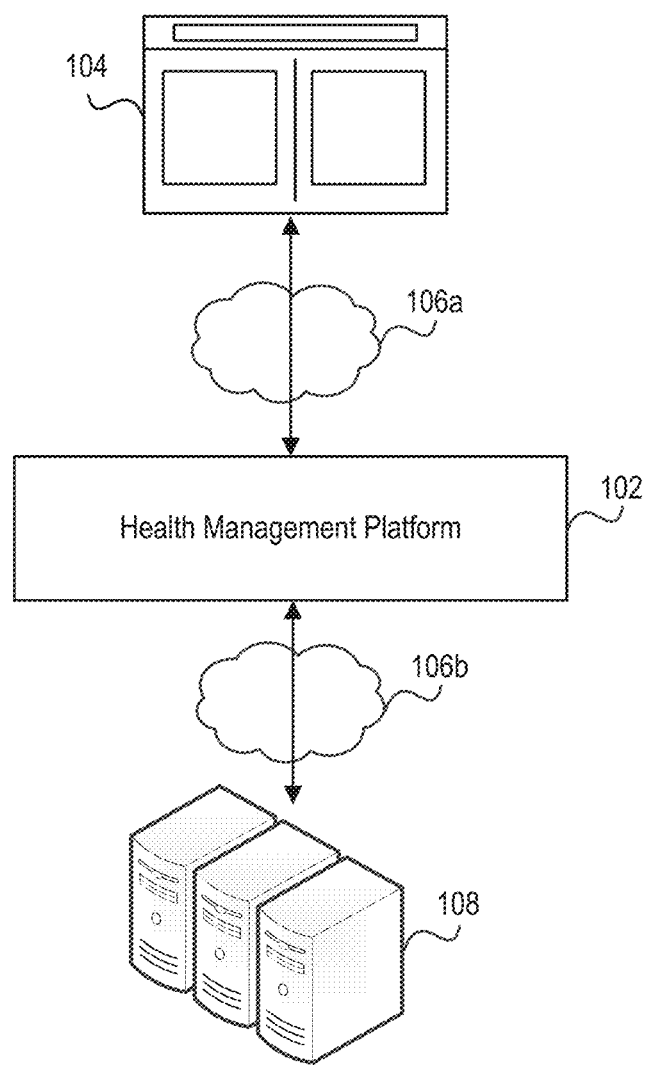
FIG. 1 illustrates a network environment that includes a health management platform.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Ubiquitous use of electronic devices, particularly in the context of social media, is known to be negatively linked with physical, mental, and emotional health. Accordingly, entities have begun developing healthcare-focused computer programs that can automatically identify, monitor, and promote different aspects of physical, mental, and emotional well-being. Some computer programs expressly solicit feedback directly from individuals (also referred to as "subjects" or "patients"), for example, via manually populated forms. Other computer programs continually track behavior along multiple dimensions without requiring input from the individuals. For example, a computer program may monitor interactions with a social media application that resides on a mobile phone. As another example, a computer program may monitor interactions with a calling application or a messaging application that resides on a mobile phone.

Classification algorithms can then be applied by the computer program to detect deviations from routine patterns. A classification algorithm may be designed to identify deviations in the frequency with which an individual interacts with an application, the time spent interacting with the application, the digital activities performed using the application, etc. By applying the classification algorithms, the computer program can automatically assess the health state based on health characteristics inferred from these behaviors. Health characteristics can include, for example, estimated sleep duration, physical activities, communication activities, and social interactions.

However, these computer programs cannot capture much of the contextual resolution necessary to fully understand the health implications of various stimuli. For instance, little is known about which stimuli presented by an electronic device actually cause an individual to experience physiological responses, either positive or negative. Consequently, actions cannot be taken to actively prevent the individual from performing those activities that negatively impact the health state. Similarly, actions cannot be taken to actively encourage the individual to perform those activities that positively impact the health state.

Introduced here, therefore, are health management platforms able to monitor changes in the health state of an individual based on the context of digital activities performed by, or involving, the individual. More specifically, a health management platform can examine physiological data associated with an individual to identify a physiological response (also referred to as a "physiological event") and then identify a stimulus presented by an electronic device that caused the physiological response. The term "stimulus" can refer to any digital content shown by the electronic device or any digital activity involving the electronic device.

The physiological response may correspond to one or more values in the physiological data that exceed a predetermined threshold, match a predetermined pattern, etc. In some embodiments, the individual is prompted to specify whether the physiological response is a positive physiological response or a negative physiological response. Thus, the individual may provide feedback that indicates whether the stimulus resulted in an upward shift in health or a downward shift in health. Physiological responses that result in upward shifts in health may be referred to as "positive physiological responses," while physiological responses that result in downward shifts in health may be referred to as "negative physiological responses." The terms "health" and "health state," meanwhile, can refer to physical health, mental health, emotional health, or any combination thereof.

Appropriate action(s) can then be taken by the health management platform based on the physiological response. For example, if the individual specifies that the physiological response resulted in an upward shift in health, then the health management platform may promote future exposure to the stimulus. Conversely, if the individual specifies that the physiological response resulted in a downward shift in health, then the health management platform may inhibit future exposure to the stimulus.

A health management platform can be configured to monitor physiological data to detect heightened physiologic responses in real time. For example, the physiological data may be generated by an electronic device (e.g., a watch or a fitness tracker) that transmits the physiological data to the health management platform as it is generated. By examining the physiological data, the health management platform can detect variations exceeding a predetermined threshold. The predetermined threshold may be an absolute threshold or a relative threshold. For example, in the case of an absolute threshold, a variation may take the physiological beyond a given value. In the case of a relative threshold, the amount of variation from a baseline value or a baseline range may exceed a given amount. These variations (also referred to as "heightened physiological responses") may correspond to increases/decreases in pulse rate, electrodermal activity (EDA), skin temperature, sweat level, blood glucose level, blood pressure, disturbance during sleep, bowel movement, neurological activity, a measure that is any combination thereof, etc.

Upon detecting a heightened physiological response, the health management platform can examine contextual data to detect the stimulus responsible for provoking the heightened physiological response. As further described below, the health management platform generates a signal that prompts the electronic device on which the stimulus is presented to capture a screenshot. In some embodiments, the health management platform examines the screenshot to detect a characteristic of the stimulus. Such action may allow the health management platform to generate a digital record that links the heightened physiological response to the stimulus, characteristic, or any combination thereof.

The physiological and contextual data can be acquired from one or more different sources. In some embodiments, the physiological and contextual data are acquired from a single electronic device. For example, a watch can be programmed to generate physiological data related to a physiological feature, as well as contextual data related to stimuli presented by the watch. In other embodiments, the physiological and contextual data are acquired from multiple electronic devices. For example, a watch can be programmed to generate physiological data related to a physiological feature and then transmit the physiological data to a health management platform that resides on a mobile phone in the form of a mobile application. Upon discovering a heightened physiological response in the physiological data, the health management platform can acquire contextual data (e.g., in the form of a screenshot) from the mobile phone on which it resides.

Each stimulus can be virtually represented as a digital record that associates the physiological response with the appropriate contextual data. Generally, each digital record specifies characteristics of the corresponding physiological response such as the magnitude of the physiological response, the time of the physiological response, the duration of the physiological response, etc. Moreover, each digital record may specify characteristics of the corresponding stimulus. For example, the health management platform may discover other individuals who were involved in a digital activity performed by the individual under examination by analyzing the content of a screenshot.

Embodiments may be described with reference to particular computer programs, system configurations, networks, etc. However, those skilled in the art will recognize that these features are equally applicable to other computer program types, system configurations, network types, etc. For example, although embodiments may be described in the context of a mobile phone that includes mobile applications with which an individual may interact, the relevant features may be embodied in other electronic devices, computer programs, etc.

Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program an electronic device to perform a process for examining physiological data pertaining to physical activities performed by an individual, parsing the physiological data to discover a physiological event, examining contextual data pertaining to digital activities performed by the individual to identify a stimulus responsible for provoking the physiological event, generating a digital record that associates the stimulus with the physiological event, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Technology Overview

FIG. 1 illustrates a network environment 100 that includes a health management platform 102. Individuals can interface with the health management platform 102 via an interface 104. The health management platform 102 may be responsible for parsing physiological data to detect physiological responses and contextual data to detect the stimuli responsible for causing the physiologic responses. Based on the detected stimuli, the health management platform 102 may also determine whether patterns of stimuli exist, estimate a health state based on the physiological responses, inhibit exposure to certain stimuli (e.g., those resulting in a regression in the health state), promote exposure to certain stimuli (e.g., those resulting in an improvement in the health state), etc. The health management platform 102 may also be responsible for creating interfaces through which the individual can view contextual data (e.g., screenshots taken by an electronic device, feedback forms, and recommendations for improving the health state), review estimations of the health state, manage preferences, etc.

Physiological data could pertain to the health state of the individual accessing the interface 104 or some other person. For example, in some embodiments the interface 104 enables a person whose health state is being monitored to view their own physiological data (or analysis of such data), while in other embodiments the interface enables an individual to view physiological data (or analysis of such data) associated with some other person. The individual may be a health coach responsible for monitoring the health state of the other person. Examples of health coaches include medical professionals (e.g., a physician, nurse, or psychiatrist), mental health counselors, family members of the other person, etc. Physiological data can specify values for a physiological feature that is continually or periodically monitored over time. Thus, the physiological data may include a time-varying series of values representative of discrete measurements of a physiological feature, such as pulse rate, electrodermal activity (EDA), skin temperature, sweat level, etc.

Contextual data, meanwhile, could pertain to stimuli presented to the individual accessing the interface 104 or some other person. Thus, in some embodiments the interface 104 enables a person whose health state is being monitored to view their own contextual data (or analysis of such data), while in other embodiments the interface an individual to view contextual data (or analysis of such data) associated with some other person. Some interfaces are configured to facilitate interactions between subjects and health coaches, while other interfaces are configured to serve as informative dashboards for subjects.

As noted above, the health management platform 102 may reside in a network environment 100. Thus, the health management platform 102 may be connected to one or more networks 106a-b. The network(s) 106a-b can include personal area networks (PANs), local area networks (LANs), wide area networks (WANs), metropolitan area networks (MANs), cellular networks, the Internet, etc. Additionally or alternatively, the health management platform 102 can be communicatively coupled to electronic device(s) over a short-range communication protocol, such as Bluetooth® or Near Field Communication (NFC).

The interface 104 is preferably accessible via a web browser, desktop application, mobile application, or over-the-top (OTT) application. Accordingly, the interface 104 may be viewed on a personal computer, tablet computer, personal digital assistant (PDA), mobile phone, game console, music player, wearable electronic device (e.g., a watch or fitness accessory), network-connected ("smart") electronic device, (e.g., a television or home assistant device), virtual/augmented reality system (e.g., a head-mounted display), or some other electronic device.

Some embodiments of the health management platform 102 are hosted locally. That is, the health management platform 102 may reside on the electronic device used to access the interface 104. For example, the health management platform 102 may be embodied as a mobile application executing on a mobile phone. Other embodiments of the health management platform 102 are executed by a cloud computing service operated by Amazon Web Services® (AWS), Google Cloud Platform™, Microsoft Azure®, or a similar technology. In such embodiments, the health management platform 102 may reside on a host computer server that is communicatively coupled to one or more content computer servers 108. The content computer server(s) 108 can include media content (e.g., journal entries produced by subjects and forms populated by subjects), subject information (e.g., profiles, credentials, and health-related information such as age, mental health diagnoses, etc.), and other assets. Such information could also be stored on the host computer server.

Certain embodiments are described in the context of network-accessible interfaces. However, those skilled in the art will recognize that the interfaces need not necessarily be accessible via a network. For example, an electronic device may be configured to execute a self-contained computer program that does not require network access. Instead, the self-contained computer program may cause necessary assets (e.g., contextual data, personalized valence index, healthcare regimen data, or processing operations) to be downloaded at a single point in time or on a periodic basis (e.g., weekly, daily, or hourly).

Figure 2:
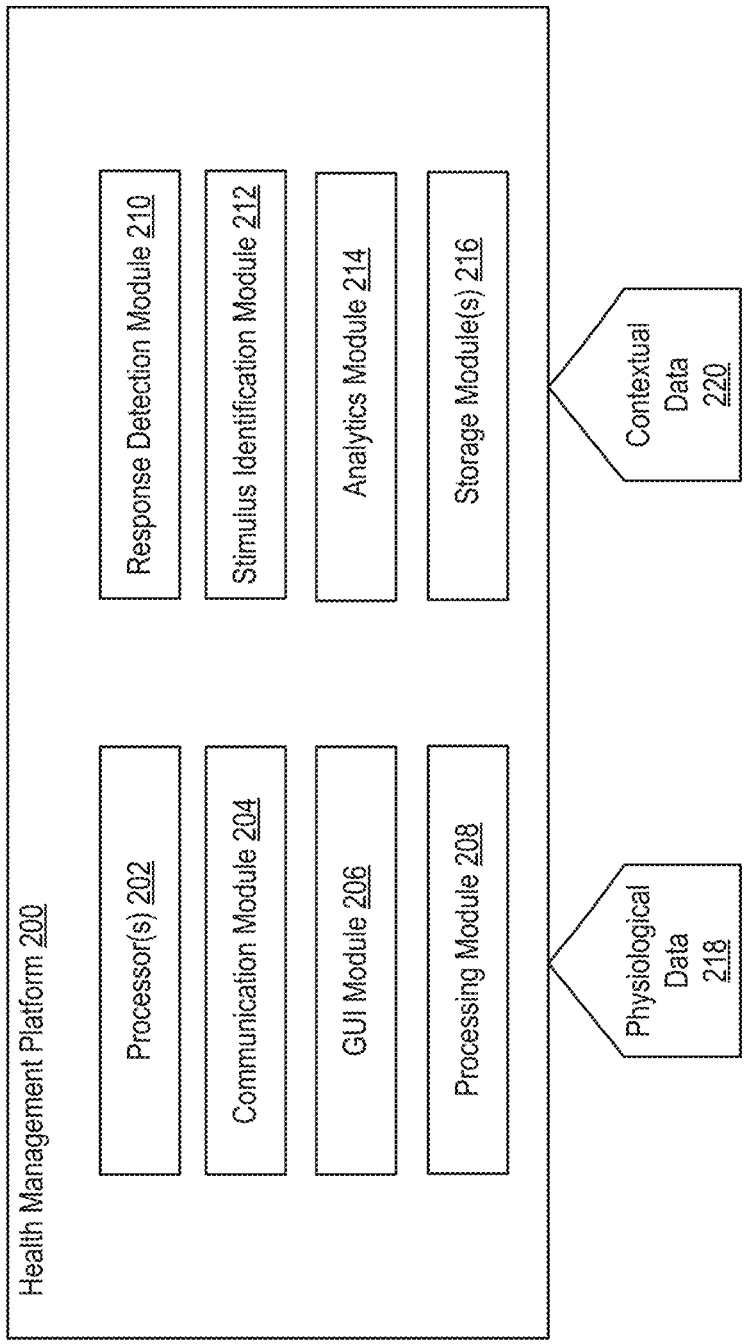
FIG. 2 depicts the high-level architecture of a health management platform able to identify stimuli that cause a subject to experience a physiological response.

FIG. 2 depicts the high-level architecture of a health management platform 200 able to identify stimuli that provoke physiological responses in a subject. The health management platform 200 may estimate the health state of the subject based on the frequency of these stimuli (or the corresponding physiological responses), as well as take certain actions to promote/inhibit the reoccurrence of certain stimuli. For example, the health management platform 200 may promote exposure to stimuli determined to have a positive effect and inhibit exposure to stimuli determined to have a negative effect. As shown in FIG. 1, an individual can interface with the health management platform 200 via an interface. The individual may be a subject whose health state is being monitored or another person with an interest in the health state of the subject.

The health management platform 200 can include one or more processors 202, a communication module 204, a graphical user interface (GUI) module 206, a processing module 208, a response detection module 210, a stimulus identification module 212, an analytics module 214, and one or more storage modules 216. In some embodiments a single storage module includes multiple computer programs for performing different operations (e.g., metadata extraction, format conversion, and feature analysis), while in other embodiments each computer program is hosted within a separate storage module. Embodiments of the health management platform 200 may include some or all of these components, as well as other components not shown here.

The processor(s) 202 can execute modules from instructions stored in the storage module(s) 216, which can be any device or mechanism capable of storing information. For example, the processor(s) 202 may execute the GUI module 206, processing module 208, response detection module 210, stimulus identification module 212, and analytics module 214.

The communication module 204 can manage communications between various components of the health management platform 200. The communication module 204 can also manage communications between the electronic device on which the health management platform 200 resides and another electronic device.

For example, the health management platform 200 may reside on a mobile phone in the form of a mobile application. In such embodiments, the communication module 204 can facilitate communication with a network-accessible computer server responsible for supporting the mobile application. As further described below, the communication module 204 may also facilitate communication with another electronic device (e.g., a wearable electronic device configured to generate physiological data 218, such as a watch, fitness tracker, etc.). The communication module 204 may facilitate communication with various data sources through the use of application programming interfaces (APIs), bulk data interfaces, etc. Examples of data sources include network-accessible databases, other mobile applications residing on the mobile phone, other electronic devices, etc.

As another example, the health management platform 200 may reside on a server system that includes one or more network-accessible computer servers. In such embodiments, the communication module 204 can communicate with a computer program executing on an electronic device associated with the individual. The components of the health management platform 200 could also be distributed between the server system and the electronic device associated with the individual in various manners. For example, some data (e.g., physiological data or contextual data) may reside on the electronic device of the individual, while other data (e.g., processing operations for detecting physiological responses, identifying stimuli, and generating a personalized stimuli index) may reside on the server system. The subject may be able to specify (e.g., via a privacy setting accessible on the electronic device) which data, if any, is transmitted to the server system, made accessible to the server system, etc. For example, the subject may be permitted to specify that the health management platform 200 can only examine screenshots that the subject has chosen to upload to the server system. As another example, the subject may be permitted to specify that the health management platform 200 can only upload screenshots of certain computer programs (e.g., social media applications) to the server system.

The GUI module 206 can generate the interface(s) through which an individual can interact with the health management platform 200. For example, an interface may include representative screenshots depicting the stimuli that resulted in heightened physiological responses over a certain period of time. As another example, an interface may include a recommendation regarding the exposure to certain stimuli. For instance, the interface may recommend that an individual avoid a stimulus in response to determining that the individual specified the stimulus caused a downward shift in mood or emotion (also referred to as "negative valence"). Similarly, the interface may recommend that an individual reexperience a stimulus in response to determining that the individual specified the stimulus caused an upward shift in mood or emotion (also referred to as "positive valence").

The processing module 208 can apply one or more operations to physiological data 218 and contextual data 220 acquired by the health management platform 200. As further described below, the physiological data 218 and contextual data 220 could be acquired from one or more sources. Examples of sources include the electronic device on which the health management platform 200 resides, a computer program executing on the electronic device, and some other electronic device. Physiological data 218 and contextual data 220 may be acquired by the health management platform 200 from different sources. Thus, the processing module 208 may apply operation(s) to the physiological data 218 and contextual data 220 to ensure that these data are in a compatible format, temporally aligned, etc.

A source may be configured to continuously or periodically transmit physiological data 218 and/or contextual data 220 to the health management platform 200. In some embodiments, a source continually uploads physiological data 218 to the health management platform 200 so long as the source remains communicatively coupled to the electronic device on which the health management platform 200 resides (e.g., via a Bluetooth® communication channel). In other embodiments, the source uploads physiological data 218 to the health management platform 200 on a periodic basis (e.g., hourly, daily, or weekly). The health management platform 200 can be configured to pull physiological data 218 and/or contextual data 220 from the source. Additionally or alternatively, the source can be configured to push physiological data 218 and/or contextual data 220 to the health management platform 200. In some embodiments, the subject or an administrator (e.g., a health coach or an individual responsible for supporting the health management platform 200) is able to configure these push/pull settings. These settings can be configured on an individual basis or a group basis (e.g., for multiple subjects that share a health characteristic in common).

The processing module 208 can process the physiological data 218 and/or the contextual data 220 into a format suitable for the other modules (e.g., the response detection module 210, stimulus identification module 212, analytics module 214, or storage module(s) 216).

The response detection module 210 can examine the physiological data 218 to identify variations that exceed a predetermined threshold or match a predetermined pattern. These variations may be referred to as "physiological responses." A first electronic device can continually monitor a physiological feature associated with a subject, thereby generating physiological data 218. The first electronic device may be, for example, a watch, fitness tracker, etc.

Thus, a watch may generate physiological data 218 that includes values for a physiological feature, such as pulse rate, electrodermal activity (EDA), skin temperature, sweat level, etc. The physiological data 218 can then be transmitted (e.g., in real time) to the health management platform 200, which, as noted above, may reside on another electronic device (e.g., a mobile phone).

After detecting a physiological response in the physiological data 218, the response detection module 210 may transmit a signal to the stimulus identification module 212. Receipt of the signal may prompt the stimulus identification module 212 to parse the contextual data 220 to identify the stimulus responsible for causing the heightened physiological response. For example, the stimulus identification module 212 may cause a screenshot to be captured by a second electronic device in use during the heightened physiological response. As another example, the stimulus identification module 212 may examine a collection of screenshots captured on a periodic basis to identify a screenshot captured within proximity of the heightened physiological response. As another example, the stimulus identification module 212 may monitor a log of computer software executing on the second electronic device, a history of websites browsed on the second electronic device, etc. The second electronic device may be, for example, a mobile phone, tablet computer, etc.

The analytics module 214 may generate a digital record for each heightened physiological response. Each digital record may associate a physiological response with the corresponding stimulus, as well as specify the magnitude of the physiological response, the time of the physiological response, the duration of the physiological response, etc. Moreover, the analytics module 214 may examine the physiological responses and/or the corresponding stimuli to determine whether any patterns exist. If a pattern is detected, the analytics module 214 may prompt the subject (or some other person, such as a health coach) to specify whether exposure to the corresponding stimulus should be limited. For example, if the analytics module 214 discovers that heightened physiologic responses occur whenever the subject accesses a particular social media account, then the analytics module 214 may recommend that the particular social media account be unfollowed, limit access to the particular social media account, etc. The analytics module 214 may also provide real-time feedback about the physiologic responses to different triggers, thereby allowing the subject to stop what she is doing in the moment.

Figure 3A:
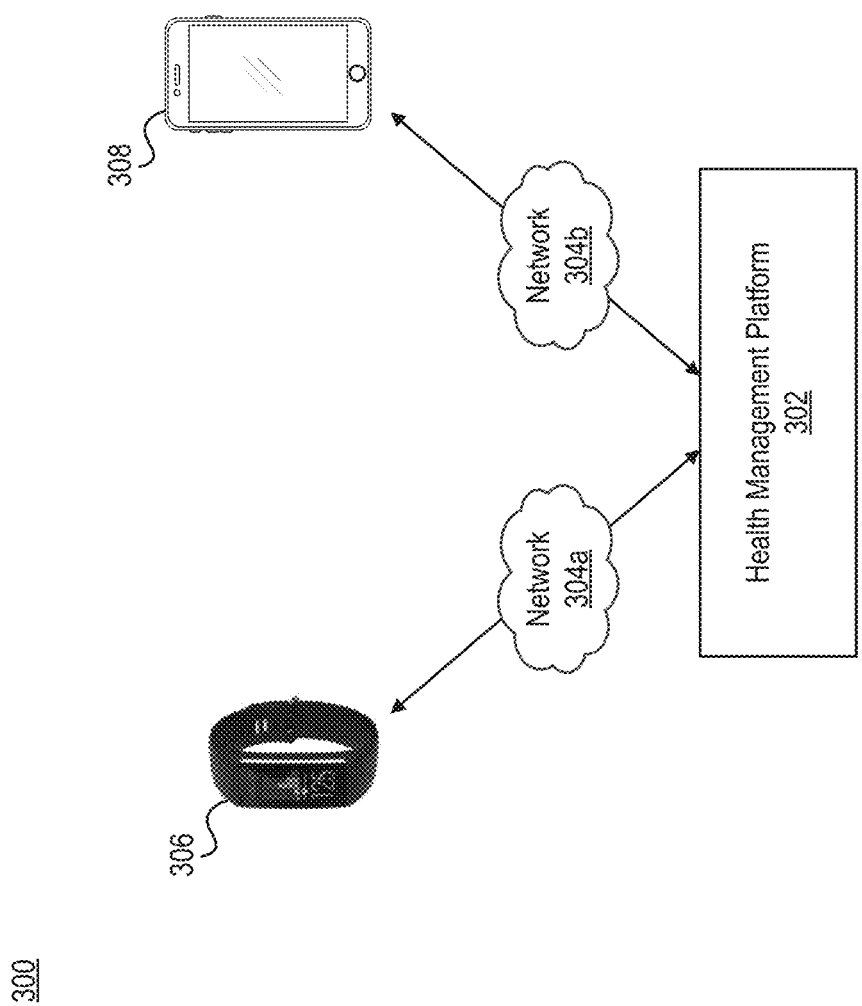
FIG. 3A depicts an example of a communication environment that includes a health management platform configured to receive physiological data and contextual data from different electronic devices.

FIG. 3A depicts an example of a communication environment 300 that includes a health management platform 302 configured to receive physiological data and contextual data from different electronic devices. Here, for example, the health management platform 302 receives physiological data from a first electronic device 306 (here, a fitness tracker) and contextual data from a second electronic device 308 (here, a mobile phone). The first electronic device 306 and the second electronic device 308 may collectively be referred to as the "networked devices."

The networked devices can be connected to the health management platform 302 via one or more computer networks 304*a-b*. The computer network(s) 304*a-b* can include PANs, LANs, WANs, MANs, cellular networks, the Internet, etc. Additionally or alternatively, the networked devices may communicate with one another over a short-range communication protocol, such as Bluetooth® or Near Field Communication (NFC). For example, the health management platform 302 may reside on the mobile phone 308 (e.g., in the form of a mobile application). In such embodiments, contextual data received from the mobile phone 308 need not traverse any computer networks. However, the mobile phone 308 may be communicatively coupled to the fitness tracker 306 via a Bluetooth® communication channel or a Wi-Fi communication channel.

Embodiments of the communication environment 300 may include some or all of the networked devices. For example, some embodiments of the communication environment 300 include a health management platform 302 that receives physiological data and contextual data from a single electronic device (e.g., the mobile phone 308 on which the health management platform 302 resides). As another example, some embodiments of the communication environment 300 include a health management platform 302 that receives contextual data from multiple sources (e.g., the mobile phone 308 and another electronic device, such as a tablet computer, network-connected television, gaming console, etc.).

Figure 3B:
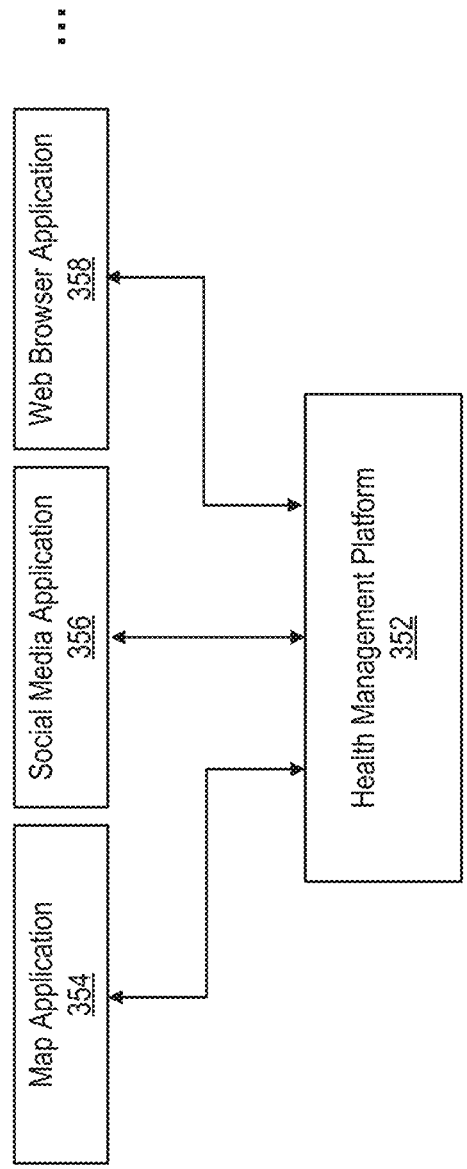
FIG. 3B depicts another example of a communication environment that includes a health management platform configured to receive contextual data from several different computer programs.

FIG. 3B depicts another example of a communication environment 350 that includes a health management platform 352 configured to receive contextual data from several different computer programs. Here, for example, the health management platform 352 receives contextual data from a map application 354, social media application 356, and web browser application 358. Those skilled in the art will recognize that these applications have been selected for the purpose of illustration only. Other applications (e.g., calendar applications, calling applications, messaging applications, music applications, video applications, etc.) may also be communicatively coupled to the health management platform 352. For example, a calendar application may generate contextual data specifying which scheduled appointments resulted in a heightened physiological response. As another example, a messaging application may generate contextual data specifying which individual(s) were communicating with the subject when a heightened physiological response occurred. As another example, a music application may generate contextual data specifying which song(s) were being listened to when a heightened physiological response occurred. The health management platform 352 may communicate with these computer programs through the use of APIs, bulk data interfaces, etc.

In some embodiments, the health management platform 352 identifies stimuli by examining the contextual data generated by these computer programs. In other embodiments, the health management platform 352 identifies stimuli by capturing screenshots while these computer programs are in use. Such action may enable the health management platform 352 to discover which computer program was in use during a physiological response, as well as what enterprises, objects, or individuals (e.g., as identified based on social media account, telephone number, etc.) were involved.

A health management platform can acquire contextual data regarding a variety of different activities, from a variety of different sources, etc. In some embodiments, the health management platform may acquire contextual data directly from a personal electronic device to detect parameters of software usage. For example, the health management platform could detect when a mobile application residing on a mobile phone was opened and/or closed, what activities were performed within the mobile application, etc. In some embodiments, the health management platform may acquire contextual data directly from a personal electronic device to detect activities that have been performed by an individual. For example, by parsing movement data generated by a wearable sensor, the health management platform may be able to detect occurrences of some activities (e.g., running, sitting, sleeping, or falling). In some embodiments, the health management platform may acquire contextual data directly from a network-connected electronic device (also referred to as a "networked electronic device"). For example, the health management platform may be able to detect when a network-connected television was turned on, when a network-connected oven was turned on or off, when a network-connected vehicle was turned on or off, etc. As another example, the health management platform may be able to detect when the individual arrived home, as well as what activities were performed, based on sounds (e.g., commands) detected by a network-connected, voice-enabled speaker.

Figure 4:
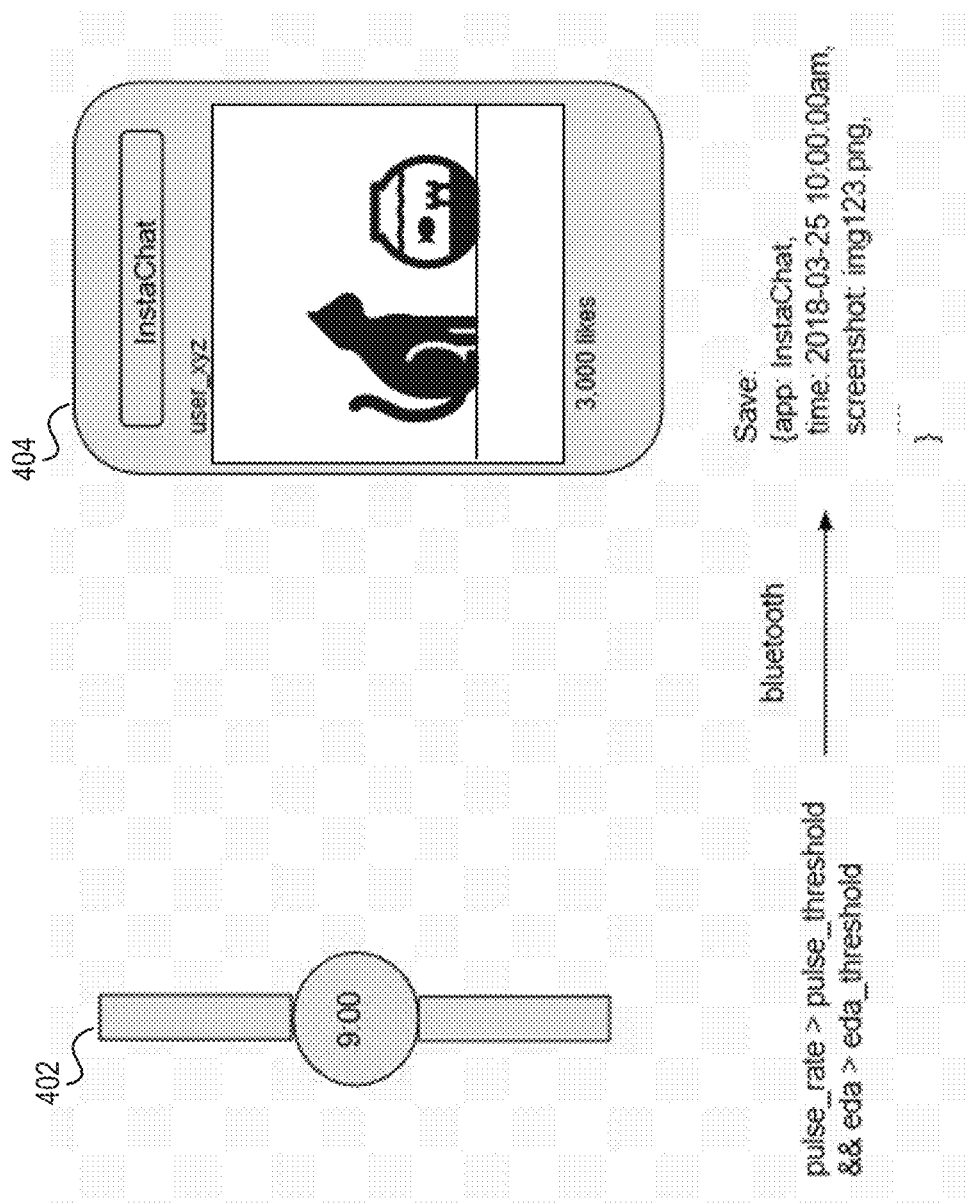
FIG. 4 includes a generalized illustration of a process for discovering a stimulus that resulted in a heightened physiological response.

FIG. 4 includes a generalized illustration of a process for discovering a stimulus that resulted in a heightened physiological response. Initially, a first electronic device 402 monitors a physiological feature associated with a subject. In some embodiments the first electronic device 402 continually monitors the physiological feature, while in other embodiments the first electronic device 402 periodically monitors the physiological feature. The first electronic device 402 may be configured to simultaneously monitor multiple physiological features. Here, for example, the first electronic device 402 monitors pulse rate and EDA.

When a heightened physiological response is discovered in physiological data generated by the first electronic device 402 by a health management platform, a signal can be provided to a second electronic device 404 responsible for presenting stimuli to the subject. Here, the heightened physiological response corresponds to a determination that the pulse rate exceeds a first predetermined threshold and the EDA exceeds a second predetermined threshold. As noted above, the health management platform may reside on the first electronic device 402 or the second electronic device 404. In embodiments where the health management platform resides on the second electronic device 404, physiological data generated by the first electronic device 402 may be streamed to the second electronic device 404 for review by the health management platform.

Upon receiving the signal, the second electronic device 404 may determine what computer software, if any, is currently in use. For example, receipt of the signal may prompt the second electronic device 404 to capture a screenshot. The health management platform can subsequently examine the screenshot to derive information about the stimulus. Moreover, the health management platform can store the screenshot and/or the information in a profile associated with the subject. The profile may be stored locally (e.g., in the first electronic device 402 or the second electronic device 404) or remotely (e.g., in a network-accessible storage accessible to the first electronic device 402 or the second electronic device 404).

FIG. 5 depicts a flow diagram of a process 500 for identifying the stimuli responsible for causing a subject to experience heightened physiological responses. A health management platform can, based on the identified stimuli, perform actions intended to improve the health of the subject. For example, the health management platform could be configured to promote exposure to digital activities associated with upward shifts in health, inhibit exposure to digital activities associated with downward shifts in health, generate personalized recommendations regarding the future performance of digital activities, etc.

Initially, a health management platform can acquire physiological data associated with a subject (step 501). The physiological data may be acquired from a wearable electronic device, such as a watch or fitness tracker, configured to monitor a physiological feature. The health management platform can then detect a physiological response (also referred to as a "physiological event") by parsing the physiological data exceeding a predetermined threshold (step 502). For example, the health management platform may discover a subset of the physiological data that corresponds to the physiological response. The physiological feature value(s) in the subset may match a predetermined pattern, exceed a predetermined threshold, or fall beneath a predetermined threshold. The health management platform may be configured to detect "negative variations" representing decreases in physiological feature values of a certain magnitude and/or "positive variations" representing increases in physiological feature values of a certain magnitude.

For instance, some embodiments of the health management platform are designed to discover patterns indicative of disturbances in sleep. In such embodiments, the health management platform may examine physiological data to identify a pattern that corresponds to a sufficiently low pulse rate (e.g., as measured by a photoplethysmography (PPG) sensor) relative to a baseline indicating that the subject is sleeping and an increase in the frequency of accelerometer peaks while the subject is sleeping. Other embodiments of the health management platform are designed to discover patterns indicative of physical activity. In such embodiments, the health management platform may examine values indicative of blood pressure as continuously measured by a blood pressure cuff device and then map those values against measurements generated by an accelerometer to discover how blood pressure changes as the subject sits, sleeps, walks, etc. Moreover, the health management platform could look for potential health events corresponding to changes in blood pressure during these activities. In these examples, the health management platform analyzes physiological data acquired from multiple sources. Note, however, that the health management platform could be configured to discover patterns in physiological data acquired from a single source. For example, the health management platform may initially detect a high-level feature indicative of whether the subject is sitting, standing, or moving by examining physiological data generated by an accelerometer, and then the health management platform could detect whether the subject's hands are shaking by reexamining the same physiological data.

In response to detecting the physiological response, the health management platform can examine contextual data associated with the subject. More specifically, the health management platform can parse the contextual data to identify a stimulus responsible for causing the physiological response (step 503). The contextual data may be indicative of an interaction by the subject with the stimulus. For instance, the contextual data may measure, quantify, or digitally portray the interaction, the stimulus, or any combination thereof. If the contextual data measures, quantifies, or portrays an interaction (e.g., by indicating when the subject accessed a given computer program), the health management platform can reference a data structure, such as a table or a database, that includes known stimuluses associated with the subject to identify which stimulus, if any, corresponds to the interaction. Thus, the health management platform may identify the stimulus responsible for causing the physiological response based on an analytical function that isolates representations of the stimulus from the contextual data and then categorizes the isolated representations into at least one type of stimulus. If the contextual data measures, quantifies, or portrays a stimulus (e.g., by identifying the location and/or individual(s) associated with an activity involving the subject), the health management platform can reference a data structure that includes known interactions involving the subject to identify which interaction, if any, corresponds to the stimulus.

The health management platform may provide privacy controls that allow the subject to limit which stimuluses, if any, will be categorized. For instance, the health management platform may permit the subject to select the stimulus(es) to be categorized from a library of stimuluses. The library of stimuluses may be related to the type of electronic device responsible for generating the contextual data. For example, if the electronic device is a mobile phone, the subject may be permitted to toggle whether the following stimuluses will be categorized: digital messaging (e.g., as a whole, or with a particular individual such as a family member or a medical professional), listening to music, communicating (e.g., via the calling application) about medication, eating (e.g., including specific types of food), alarms, indications of when sleep began and/or ended, geographical stimuluses (e.g., going to work, going home, going to school, going to a hospital), receiving a digital achievement associated with a health-related milestone, etc.

For example, the health management platform may prompt an electronic device (e.g., a mobile phone) to capture a screenshot in conjunction with the physiological response. By examining the screenshot, the health management platform can discover the stimulus responsible for provoking the physiological response. The screenshot may be captured responsive to receiving input indicative of a user action (e.g., indicating an interest in a photo, initiating a call, sending a text message), explicit user approval, a specified user privacy setting, etc. As another example, the health management platform may examine a log of software access events maintained on the electronic device to discover which computer program was open when the subject experienced the physiological response. For instance, a mobile phone may maintain a log that specifies when mobile applications were accessed, while a gaming console may maintain a log that specifies when games were accessed.

In some embodiments the stimulus is identified through basic correlation or regression, while in other embodiments the stimulus is identified through causal analysis. Regression is a statistical analysis technique for predicting a target variable (e.g., y) based on one or more other variables (e.g., $x_1$, $x_2$, etc.). Regression depends on correlation relationships between the target variable and the other variable(s), even though no causal relationship may exist. Causal analysis, meanwhile, attempts to estimate the effect of intervention (e.g., whether $x_1$ causes y). Thus, the health management platform may determine whether a given stimulus actually brings about a physiological response. In some embodiments, the health management platform records information related to the temporal relationship between the stimulus and the physiological response. Such information may be useful for further causal analysis, particularly if the causal relationship is unclear or questionable. Additionally or alternatively, the health management platform could identify the stimulus through image recognition, voice recognition, activity recognition, metadata tag searches/categorization, etc. As noted above, the health management platform may provide privacy controls that allow the subject to limit which stimuluses will be categorized (and thus which of these various identification technologies will be used by the health management platform).

In some embodiments, the health management platform is configured to create a notification that prompts the subject to provide feedback that specifies whether the physiological response corresponds to an upward or downward shift in health (step 504). The health management platform may store such information for future reference. For example, the health management platform may maintain a record of stimuli associated with upward shifts in health state. Examples of such stimuli can include posts by certain social media accounts, communications with current friends/family, etc. Similarly, the health management platform may maintain a record of stimuli associated with downward shifts in health state. Examples of such stimuli can include posts by certain social media accounts, communications with former friends/family, etc. The same stimulus could have different effects for different individuals. For example, a social media account related to a political platform may be "liked" by some individuals and "disliked" by other individuals.

Moreover, the health management platform can generate a digital record that links the stimulus, physiological response, feedback, and/or shift in health (step 505). A digital record may also associate the stimulus with physiological response characteristics such as the magnitude of the physiological response, the time of the physiological response, the duration of the physiological response, etc. The digital record may be stored in a personalized stimuli profile associated with the subject.

In some embodiments, the health management platform is configured to proactively manage the health state of the subject based on the digital records maintained in the profile. For instance, the health management platform may detect another instance of the stimulus. In such instances, the health management platform may perform an action with respect to the other instance of the stimulus based on its predicted impact on the health of the subject (step 506). The health management platform may predict the impact based on the physiological response, feedback provided by the subject, or any combination thereof. For example, if the health management platform determines that the stimulus previously resulted in an upward shift in health, then the health management platform may promote exposure of the subject to the other instance of the stimulus. Additional exposure to the stimulus may be promoted by recommending the subject perform whatever action(s) previously resulted in exposure, automatically expose the subject to the stimulus on a continual/periodic basis (e.g., by initiating a mobile application on a periodic basis, by sending a communication that includes information on positive stimuli). Conversely, if the health management platform determines that the stimulus previously resulted in a downward shift in health, then the health management platform may inhibit exposure of the subject to the other instance of the stimulus. For instance, the health management platform may automatically restrict access to a social media account associated with downward shifts in health state. Additional exposure to the stimulus may be restricted by recommending the subject refrain from performing whatever action(s) previously resulted in exposure, automatically shield the subject from exposure to the stimulus on a continua/periodic basis (e.g., by completely preventing access to a user profile for a social networking service, by restricting access to content on a social networking service by duration, access count, etc.).

In some embodiments the health management platform automatically performs the action on behalf of the subject, while in other embodiments the health management platform prompts the subject to specify whether the action should be performed. Thus, the subject may be permitted to override a recommendation to avoid certain stimuli.

FIG. 6 depicts a flow diagram of a process 600 for proactively regulating exposure to stimuli responsible for provoking physiological responses. Initially, a health management platform acquires physiological data generated by a first electronic device that monitors physical activity of a subject (step 601). Then, the health management platform can detect a physiological event by parsing the physiological data (step 602). The physiological data may include a time-varying series of values representative of discrete measurements of a physiological feature, such as pulse rate, electrodermal activity (EDA), skin temperature, sweat level, etc. Accordingly, the physiological event may be defined by value(s) that match a predetermined pattern, exceed a predetermined threshold, fall beneath a predetermined threshold, etc. In some embodiments, the physiological event is associated with multiple physiological features. For example, the health management platform may determine that a physiological event has occurred only if pulse rate exceeds a first threshold and EDA exceeds a second threshold.

The health management platform can then identify a stimulus responsible for causing the physiological event by examining contextual data generated by a second electronic device that monitors digital activity of the subject (step 603). The first and second electronic devices may be communicatively coupled to one another across a network. For example, the first electronic device may be a watch or a fitness tracker, and the second electronic device may be a mobile phone or a tablet computer. The health management platform may reside on the first electronic device, the second electronic device, or may be distributed amongst the first and second electronic devices.

In some embodiments, the health management platform generates a notification that requests an individual provide feedback indicating whether the physiological event corresponds to an upward shift in health or a downward shift in health (step 604). The individual may be the subject or a health coach responsible for managing the health of the subject. In embodiments where the individual is the subject, the notification may be presented on the first electronic device or the second electronic device. In embodiments where the individual is a health coach, the health management platform can transmit the notification to another electronic device across a network. Upon receiving the feedback from the individual (step 605), the health management platform may generate a digital record that links the stimulus, physiological response, feedback, or any combination thereof. The digital record may be stored in a personalized stimuli profile associated with the subject.

Thereafter, the health management platform may determine that another instance of the stimulus will exist for an interval of time (step 606). The health management platform may discover this other instance of the stimulus in the same batch of contextual data generated by the second electronic device or in another batch of contextual data corresponding to a different session, day, etc. In some embodiments, this other instance of the stimulus is discovered in contextual data generated by a third electronic device that monitors digital activity of the subject. For example, in embodiments where the second electronic device is a mobile phone associated with the subject, the third electronic device may be a tablet computer or a gaming console associated with the subject.

The heath management platform can perform an action with respect to this other instance of the stimulus based on the feedback received from the individual (step 607). For example, if the feedback specifies that the stimulus previously resulted in an upward shift in health, then the health management platform may promote exposure of the subject to the other instance of the stimulus. Conversely, if the feedback specifies that the stimulus previously resulted in a downward shift in health, then the health management platform may inhibit exposure of the subject to the other instance of the stimulus. For example, if the health management platform discovers that a given social media account is associated with downward shifts in health, the health management platform may automatically prevent access to the given social media account through a social media application accessible on the first, second, or third electronic device. As another example, if the health management platform discovers that a given game is associated with downward shifts in health, the health management platform may automatically limit access to the given game accessible on the first, second, or third electronic device. As another example, if the health management platform discovers that a given location is associated with downward shifts in health, the health management platform may automatically generate a notification that specifies the potential impact on health responsive to determining that the subject has entered information corresponding to the location, such as an address, into a map application.

Unless contrary to physical possibility, it is envisioned that the steps described above may be performed in various sequences and combinations. For example, the health management platform may cause an electronic device to continually or periodically generate contextual data (e.g., by capturing screenshots) regardless of whether physiological responses are detected.

Other steps may also be included in some embodiments. For example, as noted above, the health management platform may subsequently detect another instance of a stimulus determined to be responsible for causing a physiological response. The health management platform may determine that the detected stimulus is another instance of a past stimulus by matching a pattern indicative of the past stimulus, matching threshold range(s) for the corresponding contextual data, etc. For example, the health management platform may discover, upon examining the corresponding contextual data, that the detected and past stimuli correspond to a similar activity performed using the same mobile application and resulting in a similar physiological response.

As another example, the health management platform may examine a database of the digital records to detect whether any patterns exist in the physiological responses and/or stimuli. Moreover, the health management platform may notify the subject of any detected patterns, ask whether access to the corresponding stimuli should be limited, whether time-limited access constraints should be implemented, etc. For instance, if the health management platform discovers that heightened physiological responses occur whenever the subject accesses a particular social media account, then the health management platform may recommend that the particular social media account be unfollowed, or that access to the particular social media account be limited in the future. The health management platform may also provide real-time feedback about the physiological responses to different triggers, thereby allowing the subject to stop what she is doing in the moment.

Processing System

Figure 7:
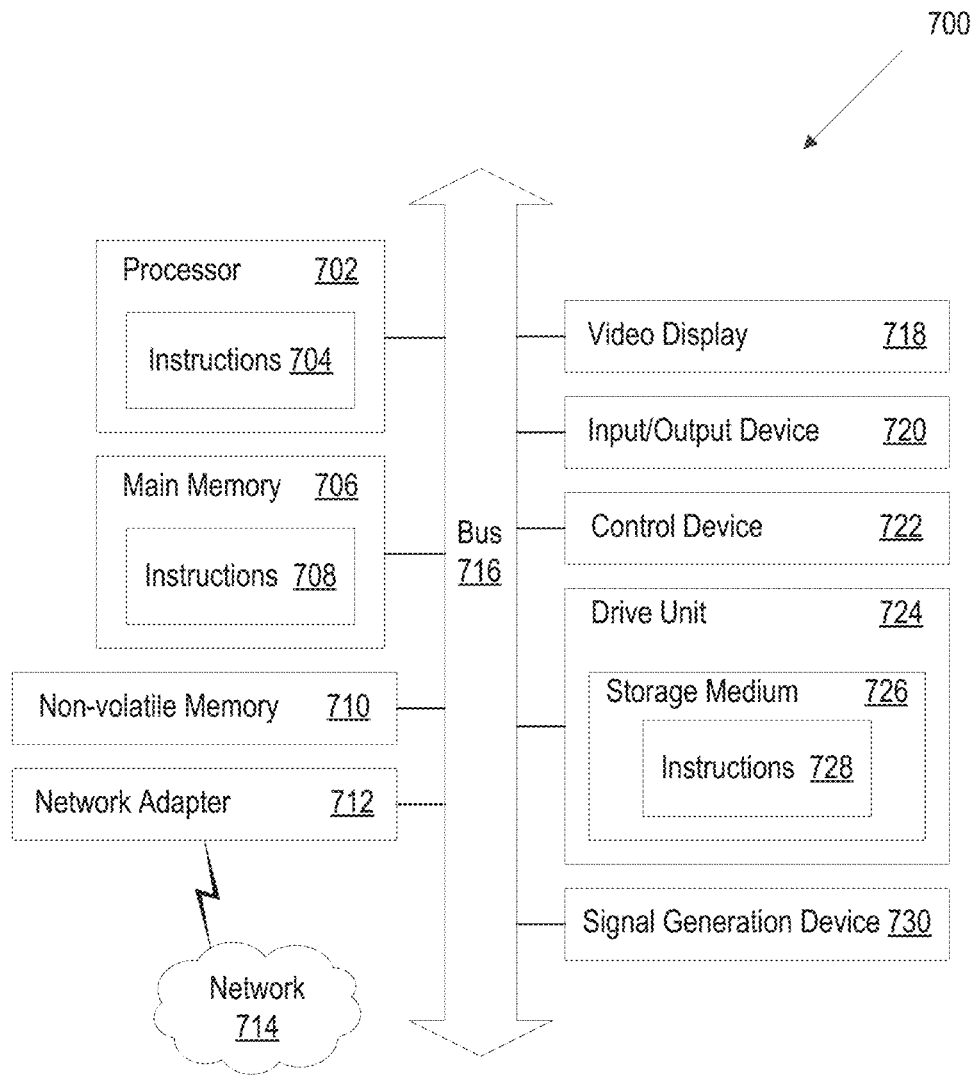
FIG. 7 is a block diagram illustrating an example of a processing system in which at least some operations described herein can be implemented.

FIG. 7 is a block diagram illustrating an example of a processing system 700 in which at least some operations described herein can be implemented. For example, some components of the processing system 700 may be hosted on an electronic device that includes a health management platform (e.g., the health management platform 102 of FIG. 1). As another example, some components of the processing system 700 may be hosted on an electronic device configured to generate physiological data and/or contextual data.

The processing system 700 may include one or more central processing units ("processors") 702, main memory 706, non-volatile memory 710, network adapter 712 (e.g., network interface), video display 718, input/output devices 720, control device 722 (e.g., keyboard and pointing devices), drive unit 724 including a storage medium 726, and signal generation device 730 that are communicatively connected to a bus 716. The bus 716 is illustrated as an abstraction that represents one or more physical buses and/or point-to-point connections that are connected by appropriate bridges, adapters, or controllers. The bus 716, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 700 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 700.

While the main memory 706, non-volatile memory 710, and storage medium 726 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 728. The term "machine-readable medium" and "storage medium" shall also be taken to include any medium that is capable of storing, encoding, or carrying a set of instructions for execution by the processing system 700.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 704, 708, 728) set at various times in various memory and storage devices in a electronic device. When read and executed by the one or more processors 702, the instruction(s) cause the processing system 700 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 710, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 712 enables the processing system 700 to mediate data in a network 714 with an entity that is external to the processing system 700 through any communication protocol supported by the processing system 700 and the external entity. The network adapter 712 can include a network adaptor card, a wireless network interface card, a router, an access point, a wireless router, a switch, a multi-layer switch, a protocol converter, a gateway, a bridge, bridge router, a hub, a digital media receiver, and/or a repeater.

The network adapter 712 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of

What is claimed is:

1. A non-transitory computer-readable medium with instructions stored thereon that, when executed by a processor, cause the processor to perform operations comprising:
acquiring physiological data generated by a first electronic device that monitors physical activity of an individual;
detecting a physiological event by parsing the physiological data to discover a subset of the physiological data that matches a predetermined pattern;
acquiring, from a second electronic device, contextual data that includes one or more screenshots documenting one or more interactions with a computer program executing on the second electronic device by the individual;
identifying, based on an analytical function, a stimulus expected to be responsible for causing the physiological event by examining the contextual data to identify a screenshot that is temporally correlated with the physiological event;
generating a digital record that associates the stimulus with the physiological event; and
storing the digital record in a personalized stimuli profile associated with the individual.

2. The non-transitory computer-readable medium of claim 1, wherein said acquiring the contextual data comprises:
generating a signal in response to detecting the physiological event; and
transmitting the signal to the second electronic device, wherein receipt of the signal causes the electronic device to capture the screenshot.

3. The non-transitory computer-readable medium of claim 1,
wherein the first electronic device is a wearable electronic device, and
wherein the second electronic device is a mobile phone.

4. The non-transitory computer-readable medium of claim 1, wherein the physiological data includes values for pulse rate, electrodermal activity, or any combination thereof.

5. The non-transitory computer-readable medium of claim 1, the operations further comprising:
generating a notification that requests the individual provide feedback indicating whether the physiological event corresponds to an upward shift in health or a downward shift in health;
transmitting the notification to the first electronic device, the second electronic device, or another electronic device accessible to the individual; and
receiving the feedback.

6. The non-transitory computer-readable medium of claim 5, the operations further comprising:
detecting another instance of the stimulus by examining the contextual data;
determining that the other instance of the stimulus will exist for an interval of time; and
performing, based on the feedback, an action with respect to the other instance of the stimulus.

7. The non-transitory computer-readable medium of claim 6,
wherein the feedback specifies that the stimulus resulted in an upward shift in health, and
wherein the action includes promoting exposure of the individual to the other instance of the stimulus.

8. The non-transitory computer-readable medium of claim 6,
wherein the feedback specifies that the stimulus resulted in a downward shift in health, and
wherein the action includes inhibiting exposure of the individual to the other instance of the stimulus.

9. The non-transitory computer-readable medium of claim 1, wherein the analytical function is configured to isolate one or more representations of the stimulus in the contextual data and categorize the one or more representations into at least one type of stimulus.

10. A computer-implemented method comprising:
acquiring, by a health management platform, physiological data generated by a first electronic device that monitors physical activity of an individual;
detecting, by the health management platform, an occurrence of a physiological event by examining the physiological data to discover one or more values that match a predetermined pattern or exceed a predetermined threshold;
acquiring, by the health management platform, contextual data generated by a second electronic device that monitors digital activities of the individual on the second electronic device,
wherein the contextual data digitally represents the digital activities;
identifying, by the health management platform, a stimulus responsible for provoking the physiological event by implementing an analytical function that examines a first portion of the contextual data that temporally corresponds to the physiological event in order to isolate a representation of the stimulus;
determining, by the health management platform, whether the physiological event corresponds to an upward shift in health or a downward shift in health;
detecting, by the health management platform, another instance of the stimulus by examining a second portion of the contextual data; and
performing, based on an outcome of said determining, an action with respect to the other instance of the stimulus.

11. The computer-implemented method of claim 10, wherein the health management platform resides on the second electronic device.

12. The computer-implemented method of claim 10, wherein the health management platform resides on a network-connected server system accessible to the second electronic device across a network.

13. The computer-implemented method of claim 10, wherein the physiological event results in an upward shift in health, and wherein said performing comprises:
promoting exposure of the individual to the other instance of the stimulus.

14. The computer-implemented method of claim 10, wherein the physiological event results in a downward shift in health, and wherein said performing comprises:
inhibiting exposure of the individual to the other instance of the stimulus.

15. The computer-implemented method of claim 10, wherein said determining comprises:

analyzing input provided by the individual that indicates whether the physiological event corresponds to an upward shift in health or a downward shift in health.

16. A computer-implemented method comprising:

acquiring, by a processor, physiological data generated by a first electronic device that monitors physical activity of an individual;

identifying, by the processor, an occurrence of a physiological event by examining the physiological data, wherein the occurrence of the physiological event corresponds to a series of values in the physiological data that match a predetermined pattern or exceed a predetermined threshold;

causing, by the processor in response to said identifying, a second electronic device to capture a screenshot of a computer program through which the individual performs a digital activity, so as to capture evidence of the digital activity performed by the individual substantially contemporaneously with identification of the physiological event experienced by the individual;

analyzing, by the processor, the screenshot to discover a characteristic of the digital activity; and generating, by the processor, a digital record that associates the physiological event with the characteristic of the digital activity.

17. The computer-implemented method of claim 16, wherein the processor resides in the second electronic device.

18. The computer-implemented method of claim 16, wherein the physiological data includes a time-varying series of values representative of discrete measurements of pulse rate, electrodermal activity (EDA), skin temperature, or sweat level.

* * * * *